United States Patent
Lim et al.

(10) Patent No.: US 11,576,896 B2
(45) Date of Patent: Feb. 14, 2023

(54) BENZOSELENOPHENE-BASED COMPOUNDS, PHARMACEUTICAL COMPOSITIONS AND ANTIBODY-DRUG CONJUGATES INCLUDING THE SAME

(71) Applicant: AIMED BIO INC., Seoul (KR)

(72) Inventors: Dongyeol Lim, Seoul (KR); Min Cheol Kim, Seoul (KR); Amol Mhetre, Seoul (KR); Do-Hyun Nam, Seoul (KR)

(73) Assignee: AIMED BIO INC., Seoul (KR)

( * ) Notice: Subject to any disclaimer, the term of this patent is extended or adjusted under 35 U.S.C. 154(b) by 129 days.

(21) Appl. No.: 17/161,771

(22) Filed: Jan. 29, 2021

(65) Prior Publication Data

US 2021/0236464 A1  Aug. 5, 2021

(30) Foreign Application Priority Data

Jan. 30, 2020 (KR) .................. 10-2020-0011222
Sep. 16, 2020 (KR) .................. 10-2020-0118786

(51) Int. Cl.
| | | |
|---|---|---|
| *A61K 31/404* | (2006.01) | |
| *A61K 47/68* | (2017.01) | |
| *A61P 35/00* | (2006.01) | |
| *A61K 47/54* | (2017.01) | |
| *C07D 421/06* | (2006.01) | |

(52) U.S. Cl.
CPC .......... *A61K 31/404* (2013.01); *A61K 47/545* (2017.08); *A61K 47/6803* (2017.08); *A61K 47/6855* (2017.08); *A61K 47/6857* (2017.08); *A61K 47/6859* (2017.08); *A61K 47/6861* (2017.08); *A61K 47/6863* (2017.08); *A61K 47/6865* (2017.08); *A61K 47/6867* (2017.08); *A61K 47/6869* (2017.08); *A61P 35/00* (2018.01); *C07D 421/06* (2013.01)

(58) Field of Classification Search
None
See application file for complete search history.

(56) References Cited

U.S. PATENT DOCUMENTS 4,975,278 A  12/1990  Senter et al.

FOREIGN PATENT DOCUMENTS

| KR | 10-2013-0034638 A | | 4/2013 |
|---|---|---|---|
| KR | 10-2017-0041562 A | | 4/2017 |
| KR | 20170041562 | * | 9/2017 |
| WO | 2007-087684 A1 | | 8/2007 |

OTHER PUBLICATIONS

Mhetre et al., RSC Adv., 2019, 9, 29023 (Year: 2019).*
Machine translation of KR 20170041562, downloaded Aug. 3, 2022 from: https://patents.google.com/patent/KR20170041562A/en?oq=%2220170041562%22 (Year: 2017).*

(Continued)

*Primary Examiner* — Karl J Puttlitz
(74) *Attorney, Agent, or Firm* — Brundidge & Stanger, P.C.

(57) ABSTRACT

The present disclosure relates to benzoselenophene-based compounds, method of preparing the benzoselenophene-based compounds, pharmaceutical compositions and antibody-drug conjugates including the benzoselenophene-based compounds.

19 Claims, 3 Drawing Sheets

(56) References Cited

OTHER PUBLICATIONS

Amol B. Mhetre et al "Synthesis and biological evaluation of potent benzoselenophene and heteroaromatic analogues of (S)-1-(chloromethyl)-8-methoxy-2,3-dihydro1H-benzo[e]indol-5-ol (seco-MCBI)," RSC Adv., Sep. 16, 2019, pp. 29023-29036.
Payne, G. "Progress in Immunoconjugate Cancer Therapeutics", Mar. 2003, Cancer Cell vol. 3: pp. 207-212.
Pamela A. Trail, et al "Monoclonal Antibody Drug Immunoconjugates for Targeted Treatment of Cancer" (2003) Cancel Immunol Immunother 52: pp. 328-337.
Syrigos KN, Epenetos AA. Antibody directed enzyme prodrug therapy (ADEPT): a review of the experimental and clinical considerations. Anticancer Research Jan.-Feb. 1999;19(1A): Abstract.
Niculescu-Duvaz and Springer, "Antibody-directed Enzyme Prodrug Therapy (ADEPT): A Review," (1997) Adv. Drug Del. Rev. 26: pp. 151-172.
International Search Report of PCT/KR2021/001082 dated May 4, 2021.
Mhetre, A. B. et al., "Synthesis and anticancer activity of benzoselenophene and heteroaromatic derivatives of 1,2,9,9a-tetrahydrocyclopropa[c]benzo[e] indol-4-one (CBI)", Organic & biomolecular chemistry, 2017, pp. 1198-1208.

\* cited by examiner

*In vitro* cell cytotoxicity assay (NCI-N87, Ez-cytox)

BENZOSELENOPHENE-BASED COMPOUNDS, PHARMACEUTICAL COMPOSITIONS AND ANTIBODY-DRUG CONJUGATES INCLUDING THE SAME

CROSS-REFERENCE TO RELATED APPLICATIONS

This application claims the benefit under 35 U.S.C. 119(a) of Korean Patent Applications No. 10-2020-0011222 filed on Jan. 30, 2020, and No. 10-2020-0118786 filed on Sep. 16, 2020, in the Korean Intellectual Property Office, the entire disclosures of which are incorporated herein by reference for all purposes.

TECHNICAL FIELD

The present disclosure relates to benzoselenophene-based compounds, method of preparing the benzoselenophene-based compounds, pharmaceutical compositions and antibody-drug conjugates including the benzoselenophene-based compounds.

BACKGROUND

Duocarmycin is known as a highly potent anticancer agent. However, duocarmycin may act as a toxin to normal cells and kill an experimental animal in the course of animal experiments. Therefore, duocarmycin itself cannot be used in humans. In this regard, studies to kill only tumor cells by tumor cell-specific response and maintain stability and high activity in blood have been actively conducted.

Antibody therapy has been used to target and treat patients with cancer, immunological disorders and angiogenic disorders. When an antibody-drug conjugate (ADC), i.e., an immunoconjugate, is used to topically deliver a drug, such as a cytotoxic agent or a cell proliferation inhibitor, that kills or suppresses tumor cells in the course of cancer treatment [References: Payne, G. (2003) Cancer Cell 3: 207-212; Trail et al (2003) Cancer Immunol. Immunother. 52:328-337; Syrigos and Epenetos (1999) Anticancer Research 19: 605-614; Niculescu-Duvaz and Springer (1997) Adv. Drug Del. Rev. 26: 151-172; U.S. Pat. No. 4,975,278], it is theoretically possible to perform targeted delivery of the drug to the tumor cells and allows the drug to accumulate within the tumor cells.

However, conventional derivatives having excellent activity are limited in water solubility and thus may aggregate when bound to a target-specific protein such as an antibody, which makes it difficult to synthesize a stable antibody-drug conjugate.

SUMMARY

In view of the foregoing, the present disclosure provides benzoselenophene-based compounds, method of preparing the benzoselenophene-based compounds, pharmaceutical compositions and antibody-drug conjugates including the benzoselenophene-based compounds.

Particularly, the present disclosure relates to preparation of a novel benzoselenophene derivative that is highly increased in water solubility and activity by introducing a novel water-soluble group to benzoselenophene and use of the benzoselenophene derivative as an anticancer drug. The novel water-soluble benzoselenophene derivative of the present disclosure can be used as an antibody-drug conjugate and can function as a prodrug. Also, the water-soluble benzoselenophene derivative can be fused to target-specific substances, such as a protein, a ligand, a nanoparticle and an aptamer, which makes it possible to function as a prodrug.

However, problems to be solved by the present disclosure are not limited to the above-described problems. Although not described herein, other problems to be solved by the present disclosure can be clearly understood by those skilled in the art from the following descriptions.

A first aspect of the present disclosure provides a benzoselenophene-based compound, represented by the following Chemical Formula 1:

[Chemical Formula 1]

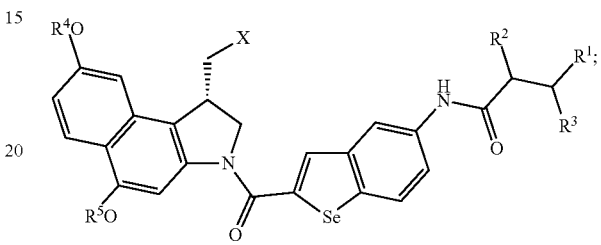

in the above Chemical Formula 1, $R^1$ is a substituted or unsubstituted amino group, or a substituted or unsubstituted linear or branched $C_{1-6}$ alkylamino group, each of $R^2$ and $R^3$ is independently hydrogen, fluorine, chlorine, bromine, iodine, or a substituted or unsubstituted $C_{1-5}$ alkyl group, each of $R^4$ and $R^5$ is independently hydrogen, or a substituted or unsubstituted $C_{1-5}$ alkyl group, and X is halogen.

A second aspect of the present disclosure provides a method of a benzoselenophene-based compound, including (a) reacting a carboxylic acid represented by the following Chemical Formula 2 with an amine represented by the following Chemical Formula 3 to prepare an intermediate product; and (b) reacting the intermediate product with an amine represented by the following Chemical Formula 4 to obtain a benzoselenophene-based compound represented by the following Chemical Formula 1:

[Chemical Formula 1]

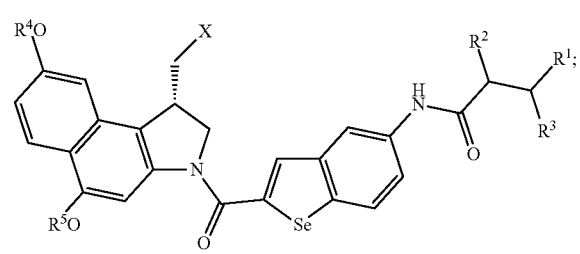

[Chemical Formula 2]

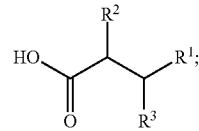

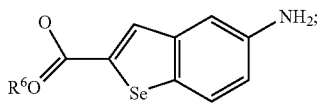

[Chemical Formula 3]

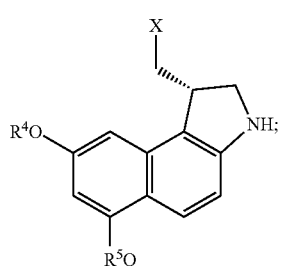

[Chemical Formula 4]

in the above Chemical Formula 1, Chemical Formula 2, Chemical Formula 3 and Chemical Formula 4, $R^1$ is a substituted or unsubstituted amino group, or a substituted or unsubstituted linear or branched $C_{1-6}$ alkylamino group, each of $R^2$ and $R^3$ is independently hydrogen, fluorine, chlorine, bromine, iodine, or a substituted or unsubstituted $C_{1-5}$ alkyl group, each of $R^4$ and $R^5$ is independently hydrogen, or a substituted or unsubstituted $C_{1-5}$ alkyl group, $R^6$ is a substituted or unsubstituted C1-5 alkyl group, and X is halogen.

A third aspect of the present disclosure provides a pharmaceutical composition, including a benzoselenophene-based compound represented by the following Chemical Formula 1 or a pharmaceutically acceptable salt thereof, and the pharmaceutical composition is for preventing or treating proliferative diseases:

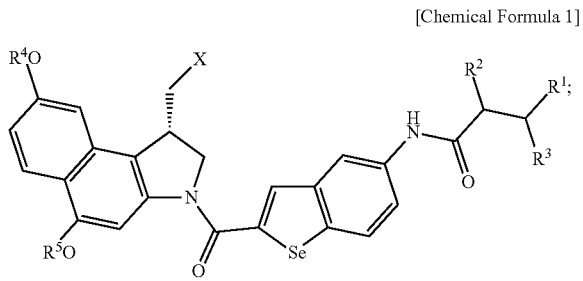

[Chemical Formula 1]

in the above Chemical Formula 1, $R^1$ is a substituted or unsubstituted amino group, or a substituted or unsubstituted linear or branched $C_{1-6}$ alkylamino group, each of $R^2$ and $R^3$ is independently hydrogen, fluorine, chlorine, bromine, iodine, or a substituted or unsubstituted $C_{1-5}$ alkyl group, each of $R^4$ and $R^5$ is independently hydrogen, or a substituted or unsubstituted $C_{1-5}$ alkyl group, and X is halogen.

A fourth aspect of the present disclosure provides an antibody-drug conjugate or a pharmaceutically acceptable salt thereof, including an antibody; a linker; and a benzoselenophene-based compound represented by the following Chemical Formula 1 or its pharmaceutically acceptable salt thereof:

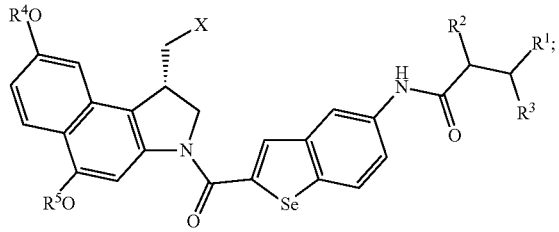

[Chemical Formula 1]

in the above Chemical Formula 1, $R^1$ is a substituted or unsubstituted amino group, or a substituted or unsubstituted linear or branched $C_{1-6}$ alkylamino group, each of $R^2$ and $R^3$ is independently hydrogen, fluorine, chlorine, bromine, iodine, or a substituted or unsubstituted $C_{1-5}$ alkyl group, each of $R^4$ and $R^5$ is independently hydrogen, or a substituted or unsubstituted $C_{1-5}$ alkyl group, and X is halogen.

A fifth aspect of the present disclosure provides an anticancer composition including the antibody-drug conjugate or a pharmaceutically acceptable salt thereof according to the fourth aspect.

BRIEF DESCRIPTION OF THE DRAWINGS

In the detailed description that follows, embodiments are described as illustrations only since various changes and modifications will become apparent to those skilled in the art from the following detailed description. The use of the same reference numbers in different figures indicates similar or identical items.

EFFECTS OF THE INVENTION

Figure 1:
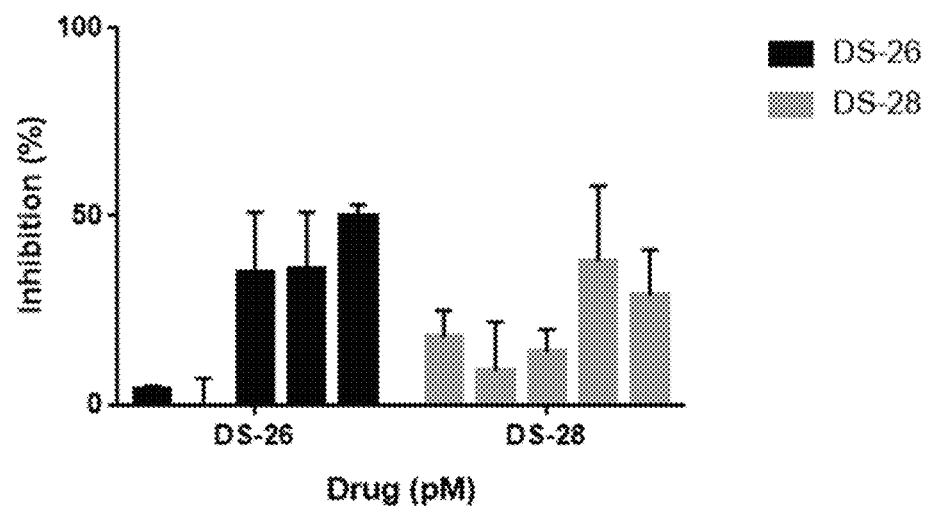
FIG. 1 is a graph showing the result of in in-vitro cytotoxicity test for substances according to an example and a comparative example of the present disclosure.
Figure 2A:
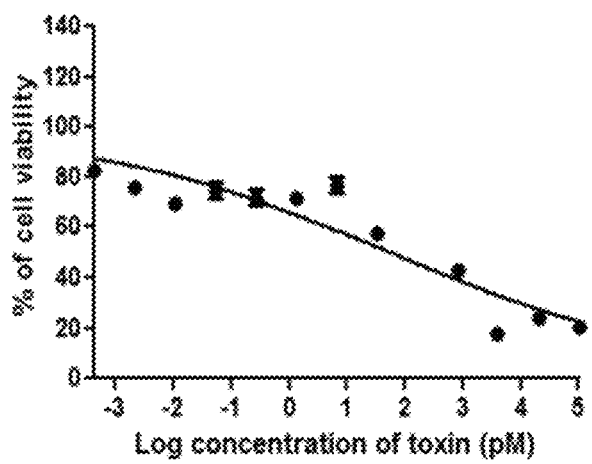
FIG. 2A and FIG. 2B show the results of cytotoxicity screening of respective substances according to Example 1 and Comparative Example 1 on NCI-N87 cells.
Figure 2B:
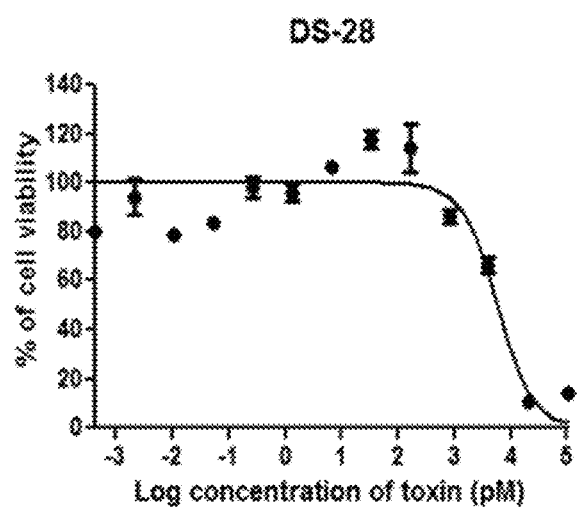
Figure 3A:
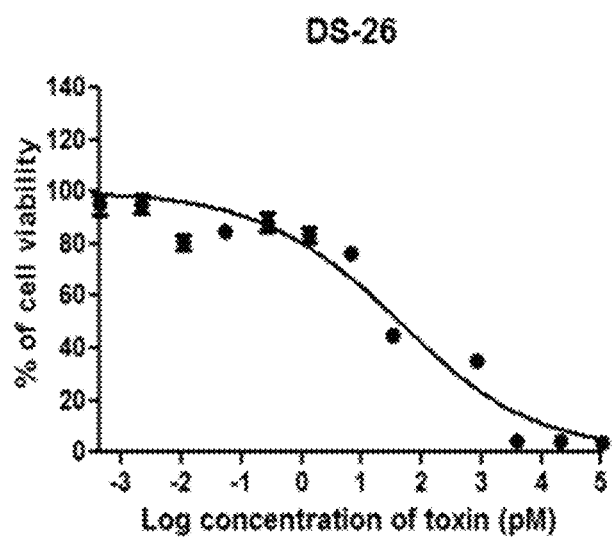
FIG. 3A and FIG. 3B show the results of cytotoxicity screening of the respective substances according to Example 1 and Comparative Example 1 on SK-OV-3 cells.
Figure 3B:
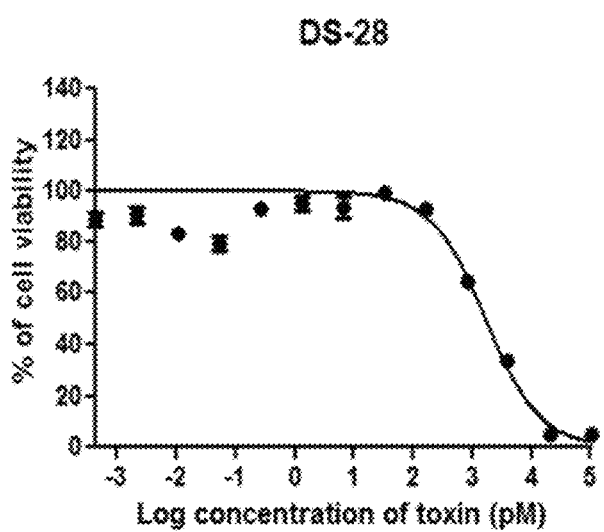

According to the embodiments of the present disclosure, it is possible to prepare a novel benzoselenophene derivative that is highly increased in water solubility and activity by introducing a novel water-soluble group from an amino group or an alkylamino group, and the benzoselenophene derivative can be used as an anticancer drug. The novel water-soluble benzoselenophene derivative of the present disclosure can be used as an antibody-drug conjugate and can function as a prodrug. Also, the water-soluble benzoselenophene derivative can be fused to target-specific substances, such as a protein, a ligand, a nanoparticle and an aptamer, which makes it possible to function as a prodrug.

According to the embodiments of the present disclosure, benzoselenophene-based compounds are substances having highly potent anticancer effect with $IC_{50}$ to cancer cells in the range of nM or pM and can be applied to the development of new drugs using antibody-drug conjugates.

According to the embodiments of the present disclosure, it is possible to synthesize a DNA alkylating derivative containing a benzoselenophene-based compound excellent in water solubility and activity and apply the DNA alkylating derivative as an anticancer drug or a precursor thereof.

DETAILED DESCRIPTION

Hereinafter, examples of the present disclosure will be described in detail with reference to the accompanying drawings so that the present disclosure may be readily implemented by those skilled in the art. However, it is to be noted that the present disclosure is not limited to the examples but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element.

Through the whole document, the term "on" that is used to designate a position of one element with respect to another element includes both a case that the one element is adjacent to the other element and a case that any other element exists between these two elements.

Further, through the whole document, the term "comprises or includes" and/or "comprising or including" used in the document means that one or more other components, steps, operation and/or existence or addition of elements are not excluded in addition to the described components, steps, operation and/or elements unless context dictates otherwise.

Through the whole document, the term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party.

Through the whole document, the term "step of" does not mean "step for".

Through the whole document, the term "combination of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Through this whole specification, a phrase in the form "A and/or B" means "A or B, or A and B".

Through the whole document, the term "alkyl" includes linear or branched alkyl groups having 1 to 12 carbon atoms, 1 to 10 carbon atoms, 1 to 8 carbon atoms, 1 to 5 carbon atoms, or 1 to 4 carbon atoms and all the possible isomers thereof. For example, the alkyl group may include methyl group (Me), ethyl group (Et), n-propyl group ($^n$Pr), iso-propyl group ($^i$Pr), n-butyl group ($^n$Bu), tert-butyl group ($^t$Bu), iso-butyl group ($^i$Bu), sec-butyl group ($^s$Bu), pentyl group, hexyl group, iso-hexyl group, heptyl group, 4,4-dimethyl pentyl group, octyl group, 2,2,4-trimethyl pentyl group, nonyl group, decyl group, undecyl group, dodecyl group, and isomers thereof, but may not be limited thereto.

Hereinafter, embodiments and examples of the present disclosure will be described in detail with reference to the accompanying drawings. However, the present disclosure may not be limited to the following embodiments, examples, and drawings.

A first aspect of the present disclosure provides a benzoselenophene-based compound, represented by the following Chemical Formula 1:

[Chemical Formula 1]

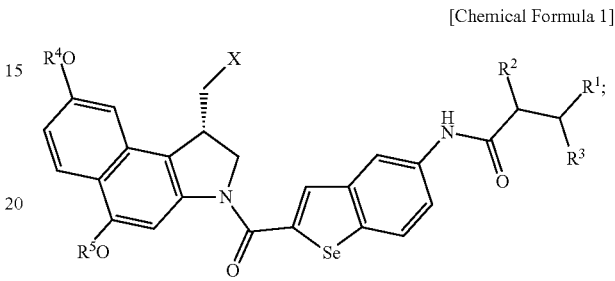

in the above Chemical Formula 1, $R^1$ is a substituted or unsubstituted amino group, or a substituted or unsubstituted linear or branched $C_{1-6}$ alkylamino group, each of $R^2$ and $R^3$ is independently hydrogen, fluorine, chlorine, bromine, iodine, or a substituted or unsubstituted $C_{1-5}$ alkyl group, each of $R^4$ and $R^5$ is independently hydrogen, or a substituted or unsubstituted $C_{1-5}$ alkyl group, and X is halogen.

In an embodiment of the present disclosure, if the functional groups are substituted, the substituents may include one or more members selected from an acyl group, an amino group (including mono- and dialkylamino groups, mono- and diarylamino groups and an alkylarylamino group), an acylamino group (including a carbamoyl and a ureido group), an alkylcarbonyloxy group, an arylcarbonyloxy group, an alkoxycarbonyloxy group, an alkoxycarbonyl group, a carboxyl group, a carboxylate group, an aminocarbonyl group, mono- and dialkylaminocarbonyl groups, a cyano group, an azido group, a halogen group, a hydroxyl group, a nitro group, a trifluoromethyl group, a thiol group, an alkylthiol group, an arylthiol group, an alkylthiocarbonyl group, a thiocarboxylate group, a low-grade alkyl group, a low-grade alkenyl group, a low-grade alkynyl group, a cycloalkyl group, a heterocycloalkyl group, an aryl group, a heteroaryl group, a low-grade alkoxy group, an aryloxy group, an aryloxycarbonyloxy group, a benzyloxy group, a benzyl group, a sulfinyl group, an alkylsulfinyl group, a sulfonyl group, a sulfate group, a sulfonate group, a sulfonamide group, a phosphate group, a phosphonate group, a phosphinato group, an oxo group, a guanidine group, an imino group and a formyl group, but may not be limited thereto.

In an embodiment of the present disclosure, $R^1$ may be a dialkylamino group including tertiary nitrogen, and each of $R^4$ and $R^5$ may be independently hydrogen, methyl or ethyl, but may not be limited thereto.

In an embodiment of the present disclosure, X may be F, Cl, Br or I, but may not be limited thereto. Further, in an embodiment of the present disclosure, X may be Cl.

In an embodiment of the present disclosure, a benzoselenophene-based compound of the present disclosure contains —CHR²CHR¹R³ linked to a benzoselenophene host by an amide bond and two sp³ carbon atoms as a main framework and thus can be increased in flexibility of the molecules. Further, desirably, R¹ contains tertiary amine having a small substituent. For example, if R¹ is tertiary nitrogen, since its pK$_a$ is about 6, it functions as a weak base and exists in the form of a salt under physiological conditions, which may cause a great increase in water solubility.

In an embodiment of the present disclosure, R¹ includes dimethylamino, ethylmethylamino, diethylamino, methylpropylamino, ethylpropylamino or dipropylamino, but may not be limited thereto.

In an embodiment of the present disclosure, R¹ may be dimethylamino, ethylmethylamino, diethylamino.

In an embodiment of the present disclosure, both of R² and R³ may be hydrogen.

In an embodiment of the present disclosure, each of R⁵ and R⁶ may be independently hydrogen, methyl, ethyl or propyl.

In an embodiment of the present disclosure, the benzoselenophene-based compound may include the following compound 2:

[Compound 2]

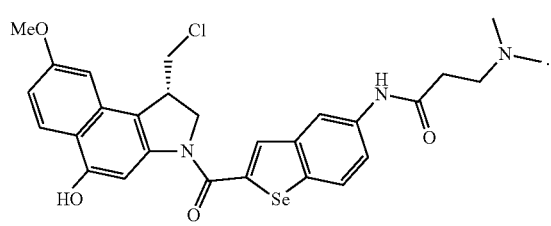

A second aspect of the present disclosure provides a method of a benzoselenophene-based compound, including (a) reacting a carboxylic acid represented by the following Chemical Formula 2 with an amine represented by the following Chemical Formula 3 to prepare an intermediate product; and (b) reacting the intermediate product with an amine represented by the following Chemical Formula 4 to obtain a benzoselenophene-based compound represented by the following Chemical Formula 1:

[Chemical Formula 1]

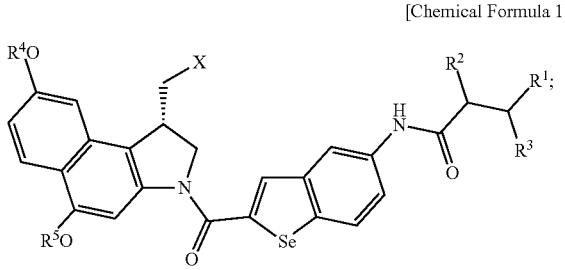

[Chemical Formula 2]

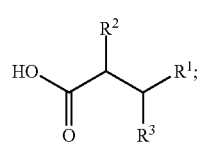

[Chemical Formula 3]

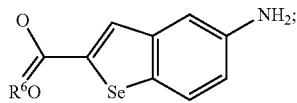

[Chemical Formula 4]

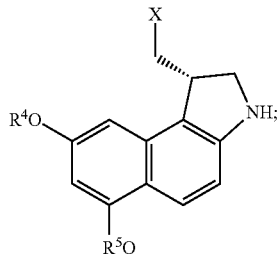

in the above Chemical Formula 1, Chemical Formula 2, Chemical Formula 3 and Chemical Formula 4, R¹ is a substituted or unsubstituted amino group, or a substituted or unsubstituted linear or branched $C_{1-6}$ alkylamino group, each of R² and R³ is independently hydrogen, fluorine, chlorine, bromine, iodine, or a substituted or unsubstituted $C_{1-5}$ alkyl group, each of R⁴ and R⁵ is independently hydrogen, or a substituted or unsubstituted $C_{1-5}$ alkyl group, R⁶ is a substituted or unsubstituted C1-5 alkyl group, and X is halogen.

Detailed descriptions on the second aspect of the present disclosure, which overlap with those on the first aspect of the present disclosure, are omitted hereinafter, but the descriptions of the first aspect of the present disclosure may be identically applied to the second aspect of the present disclosure, even though they are omitted hereinafter.

In an embodiment of the present disclosure, if the functional groups are substituted, the substituents may include one or more members selected from an acyl group, an amino group (including mono- and dialkylamino groups, mono- and diarylamino groups and an alkylarylamino group), an acylamino group (including a carbamoyl and a ureido group), an alkylcarbonyloxy group, an arylcarbonyloxy group, an alkoxycarbonyloxy group, an alkoxycarbonyl group, a carboxyl group, a carboxylate group, an aminocarbonyl group, mono- and dialkylaminocarbonyl groups, a cyano group, an azido group, a halogen group, a hydroxyl group, a nitro group, a trifluoromethyl group, a thiol group, an alkylthiol group, an arylthiol group, an alkylthiocarbonyl group, a thiocarboxylate group, a low-grade alkyl group, a low-grade alkenyl group, a low-grade alkynyl group, a cycloalkyl group, a heterocycloalkyl group, an aryl group, a heteroaryl group, a low-grade alkoxy group, an aryloxy group, an aryloxycarbonyloxy group, a benzyloxy group, a benzyl group, a sulfinyl group, an alkylsulfinyl group, a sulfonyl group, a sulfate group, a sulfonate group, a sulfonamide group, a phosphate group, a phosphonate group, a phosphinato group, an oxo group, a guanidine group, an imino group and a formyl group, but may not be limited thereto.

In an embodiment of the present disclosure, R¹ may be a dialkylamino group including tertiary nitrogen, and each of $R^4$ and $R^5$ may be independently hydrogen, methyl or ethyl, but may not be limited thereto.

In an embodiment of the present disclosure, X may be F, Cl, Br or I, but may not be limited thereto. Further, in an embodiment of the present disclosure, X may be Cl.

In an embodiment of the present disclosure, a benzoselenophene-based compound of the present disclosure contains —$CHR^2CHR^1R^3$ linked to a benzoselenophene host by an amide bond and two $sp^3$ carbon atoms as a main framework and thus can be increased in flexibility of the molecules. Further, desirably, $R^1$ contains tertiary amine having a small substituent. For example, if $R^1$ is tertiary nitrogen, since its $pK_a$ is about 6, it functions as a weak base and exists in the form of a salt under physiological conditions, which may cause a great increase in water solubility.

In an embodiment of the present disclosure, $R^1$ includes dimethylamino, ethylmethylamino, diethylamino, methylpropylamino, ethylpropylamino or dipropylamino, but may not be limited thereto.

In an embodiment of the present disclosure, $R^1$ may be dimethylamino, ethylmethylamino, diethylamino.

In an embodiment of the present disclosure, both of $R^2$ and $R^3$ may be hydrogen.

In an embodiment of the present disclosure, each of $R^5$ and $R^6$ may be independently hydrogen, methyl, ethyl or propyl.

In an embodiment of the present disclosure, the intermediate product prepared from (a) may be in a carboxylic acid form or a carboxylate salt form since $R^6$ is substituted with hydrogen by adjusting a pH, but may not be limited thereto.

In an embodiment of the present disclosure, an amine compound represented by the above Chemical Formula 4 may be obtained by performing an acid treatment on conventionally known seco-MCBI as represented below, but may not be limited thereto:

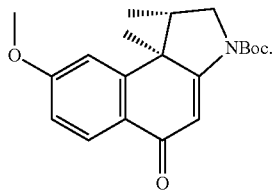 [SMILES: COc1ccc2c(c1)[C@]1(C)C(=CC2=O)N(C(=O)OC(C)(C)C)C[C@H]1C]

In an embodiment of the present disclosure, the benzoselenophene-based compound may include the following compound 2:

[Compound 2]

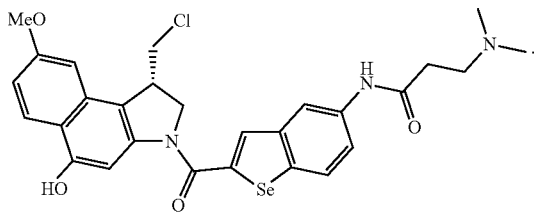 [SMILES: COc1ccc2c(O)cc3c(c2c1)[C@H](CCl)CN3C(=O)c1cc2cc(NC(=O)CCN(C)C)ccc2[se]1]

A third aspect of the present disclosure provides a pharmaceutical composition, including a benzoselenophene-based compound represented by the following Chemical Formula 1 or a pharmaceutically acceptable salt thereof, and the pharmaceutical composition is for preventing or treating proliferative diseases:

[Chemical Formula 1]

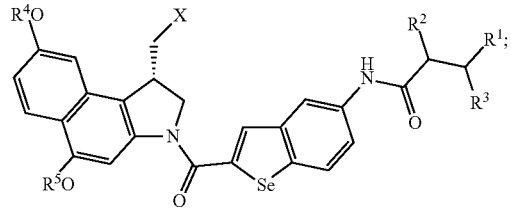

in the above Chemical Formula 1, $R^1$ is a substituted or unsubstituted amino group, or a substituted or unsubstituted linear or branched $C_{1-6}$ alkylamino group, each of $R^2$ and $R^3$ is independently hydrogen, fluorine, chlorine, bromine, iodine, or a substituted or unsubstituted $C_{1-5}$ alkyl group, each of $R^4$ and $R^5$ is independently hydrogen, or a substituted or unsubstituted $C_{1-5}$ alkyl group, and X is halogen.

Detailed descriptions on the third aspect of the present disclosure, which overlap with those on the first aspect and the second aspect of the present disclosure, are omitted hereinafter, but the descriptions of the first aspect and the second aspect of the present disclosure may be identically applied to the second aspect of the present disclosure, even though they are omitted hereinafter.

In an embodiment of the present disclosure, the benzoselenophene-based compound or the pharmaceutically acceptable salt thereof may be a prodrug, but may not be limited thereto.

In an embodiment of the present disclosure, the benzoselenophene-based compound or the pharmaceutically acceptable salt thereof may be in an active form when present within a solvent or administered into the body, but may not be limited thereto.

In an embodiment of the present disclosure, the proliferative diseases may include at least one selected from neoplasm, tumor, cancer, leukemia, psoriasis, bone diseases, fibroplasia disorders and atherosclerosis, but may not be limited thereto.

In an embodiment of the present disclosure, the cancer may include at least one selected from solid tumor, hematologic malignancy, calorectal cancer, uterine cancer, uterine myoma, meningioma, lung cancer, small cell lung cancer, gastrointestinal malignancy, colorectal cancer, intestinal cancer, breast cancer, ovarian cancer, prostate cancer, testis cancer, liver cancer, renal cancer, bladder cancer, pancreatic cancer, brain cancer, sarcoma, osteogenic sarcoma, Kaposi sarcoma and melanoma, but may not be limited thereto. A pharmaceutical composition according to an embodiment of the present disclosure can be applied to various diseases, not limited to cancers, as prevention or treatment targets.

In an embodiment of the present disclosure, if the functional groups are substituted, the substituents may include one or more members selected from an acyl group, an amino group (including mono- and dialkylamino groups, mono- and diarylamino groups and an alkylarylamino group), an acylamino group (including a carbamoyl and a ureido group), an alkylcarbonyloxy group, an arylcarbonyloxy group, an alkoxycarbonyloxy group, an alkoxycarbonyl group, a carboxyl group, a carboxylate group, an aminocarbonyl group, mono- and dialkylaminocarbonyl groups, a cyano group, an azido group, a halogen group, a hydroxyl group, a nitro group, a trifluoromethyl group, a thiol group, an alkylthiol group, an arylthiol group, an alkylthiocarbonyl group, a thiocarboxylate group, a low-grade alkyl group, a low-grade alkenyl group, a low-grade alkynyl group, a cycloalkyl group, a heterocycloalkyl group, an aryl group, a heteroaryl group, a low-grade alkoxy group, an aryloxy group, an aryloxycarbonyloxy group, a benzyloxy group, a benzyl group, a sulfinyl group, an alkylsulfinyl group, a sulfonyl group, a sulfate group, a sulfonate group, a sulfonamide group, a phosphate group, a phosphonate group, a phosphinato group, an oxo group, a guanidine group, an imino group and a formyl group, but may not be limited thereto.

In an embodiment of the present disclosure, $R^1$ may be a dialkylamino group including tertiary nitrogen, and each of $R^4$ and $R^5$ may be independently hydrogen, methyl or ethyl, but may not be limited thereto.

In an embodiment of the present disclosure, X may be F, Cl, Br or I, but may not be limited thereto. Further, in an embodiment of the present disclosure, X may be Cl.

In an embodiment of the present disclosure, a benzoselenophene-based compound of the present disclosure contains —$CHR^2CHR^1R^3$ linked to a benzoselenophene host by an amide bond and two sip' carbon atoms as a main framework and thus can be increased in flexibility of the molecules. Further, desirably, $R^1$ contains tertiary amine having a small substituent. For example, if $R^1$ is tertiary nitrogen, since its $pK_a$ is about 6, it functions as a weak base and exists in the form of a salt under physiological conditions, which may cause a great increase in water solubility.

In an embodiment of the present disclosure, $R^1$ includes dimethylamino, ethylmethylamino, diethylamino, methylpropylamino, ethylpropylamino or dipropylamino, but may not be limited thereto.

In an embodiment of the present disclosure, $R^1$ may be dimethylamino, ethylmethylamino, diethylamino.

In an embodiment of the present disclosure, both of $R^2$ and $R^3$ may be hydrogen.

In an embodiment of the present disclosure, each of $R^5$ and $R^6$ may be independently hydrogen, methyl, ethyl or propyl.

In an embodiment of the present disclosure, the benzoselenophene-based compound may include the following compound 2:

[Compound 2]

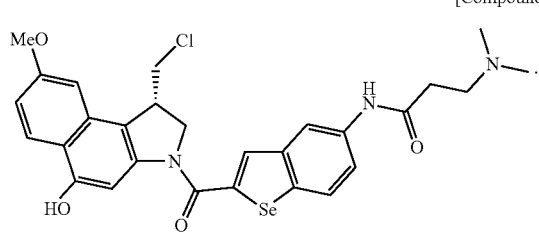

A fourth aspect of the present disclosure provides an antibody-drug conjugate or a pharmaceutically acceptable salt thereof, including an antibody; a linker; and a benzoselenophene-based compound represented by the following Chemical Formula 1 or its pharmaceutically acceptable salt thereof:

[Chemical Formula 1]

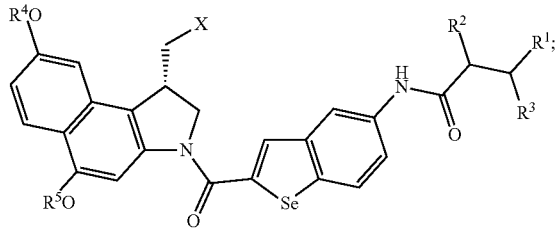

in the above Chemical Formula 1, $R^1$ is a substituted or unsubstituted amino group, or a substituted or unsubstituted linear or branched $C_{1-6}$ alkylamino group, each of $R^2$ and $R^3$ is independently hydrogen, fluorine, chlorine, bromine, iodine, or a substituted or unsubstituted $C_{1-5}$ alkyl group, each of $R^4$ and $R^5$ is independently hydrogen, or a substituted or unsubstituted $C_{1-5}$ alkyl group, and X is halogen.

Detailed descriptions on the fourth aspect of the present disclosure, which overlap with those on the first aspect to the third aspect of the present disclosure, are omitted hereinafter, but the descriptions of the first aspect to the third aspect of the present disclosure may be identically applied to the second aspect of the present disclosure, even though they are omitted hereinafter.

In an embodiment of the present disclosure, the benzoselenophene-based compound or the pharmaceutically acceptable salt thereof may be a prodrug, but may not be limited thereto.

In an embodiment of the present disclosure, the benzoselenophene-based compound or the pharmaceutically acceptable salt thereof may be in an active form when present within a solvent or administered into the body, but may not be limited thereto.

In an embodiment of the present disclosure, the antibody may include an antibody, an antibody variant or antigen-binding fragments thereof immunospecific to a proliferative disease, but may not be limited thereto. Here, the term "antibody" may encompass a polyclonal antibody and a monoclonal antibody, and desirably, it may be a monoclonal antibody and may have a whole antibody form. The whole antibody has two full-length light chains and two full-length heavy chains and includes an invariant domain, and each light chain is linked to a heavy chain by a disulfide bond. Also, in an embodiment of the present disclosure, the antibody may include a monoclonal antibody, a multispecific antibody, a human antibody, a humanized antibody, a chimeric antibody, a short chain Fvs (scFV), a short chain antibody, Fab fragments, F(ab') fragments, a disulfide-binding Fvs (dsFV) and an anti-idiotype (anti-Id) antibody, or epitope-binding fragments thereof, and the like, but may not be limited thereto. A whole anti-c-Met antibody according to embodiments of the present disclosure encompasses IgA, IgD, IgE, IgM and IgG, and IgG encompasses IgG1, IgG2, IgG3, and IgG4 as subtypes thereof. Further, the term "antibody variant" includes a double antibody, and the double antibody refers to an antibody to a single substance containing antibodies or antibody-binding fragments that recognize different antigens, respectively, and may include an antibody specific to a cancer-related antigen or an immune checkpoint protein antigen, or an antibody or antigen-binding fragment thereof which binds specifically to an immune effector cell-related antigen, but may not be limited to limited antibody frameworks. Further, the term "antigen-binding fragment" refers to a fragment having the ability to specifically bind to the antigen, and may include Fab, Fab', F(ab')2, scFv (scFv)2, scFv-Fc and Fv.

In an embodiment of the present disclosure, the proliferative diseases may include at least one selected from neoplasm, tumor, cancer, leukemia, psoriasis, bone diseases, fibroplasia disorders and atherosclerosis, but may not be limited thereto.

In an embodiment of the present disclosure, the cancer may include at least one selected from solid tumor, hematologic malignancy, calorectal cancer, uterine cancer, uterine myoma, meningioma, lung cancer, small cell lung cancer, gastrointestinal malignancy, colorectal cancer, intestinal cancer, breast cancer, ovarian cancer, prostate cancer, testis cancer, liver cancer, renal cancer, bladder cancer, pancreatic cancer, brain cancer, sarcoma, osteogenic sarcoma, Kaposi sarcoma and melanoma, but may not be limited thereto. A pharmaceutical composition according to an embodiment of the present disclosure can be applied to various diseases, not limited to cancers, as prevention or treatment targets.

In an embodiment of the present disclosure, the antibody may bind to at least one tumor-related antigens or cell surface acceptors selected from the followings, but may not be limited thereto. Also, the antibody may bind to the following various antigens that are conventionally known, but may not be limited thereto:

(1) BMPR1B (bone morphogenetic protein receptor-type 1B); (2) E16 (LAT1, SLC7A5); (3) STEAP1 (six transmembrane epithelial antigen of prostate); (4) 0772P (CA125, MUC16); (5) MPF (MPF, MSLN, SMR, megakaryocyte potentiating factor, mesothelin); (6) Napi3b [NAPI-3B, NPTIIb, SLC34A2, solute carrier family 34 (sodium phosphate), member 2, type II sodium-dependent phosphate transporter 3b]; (7) Sema 5b (F1110372, KIAA1445, Mm.42015, SEMA5B, SEMAG, Semaphorin 5b H log, sema domain, seven thrombospondin repeats (type 1 and type 1-like), transmembrane domain (TM) and short cytoplasmic domain, (semaphorin) 5B); (8) PSCA hlg (2700050C12Rik, C530008O16Rik, RIKEN cDNA 2700050C12, RIKEN cDNA 2700050C12 gene); (9) ETBR (Endothelin type B receptor); (10) MSG783 (RNF24, hypothetical protein FLJ20315); (11) STEAP2 [HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein]; (12) TrpM4 [BR22450, F1120041, TRPM4, TRPM4B, transient receptor potential cation channel, subfamily M, member 4]; (13) CRIPTO [CR, CR1, CRGF, CRIPTO, TDGF1, teratocarcinoma-derived growth factor]; (14) CD21 (CR2 (Complement receptor 2) or C3DR (C3d/Epstein Barr virus receptor) or Hs 73792; (15) CD79b (CD79B, CD79P, IGb (immunoglobulin-associated beta), B29); (16) FcRH2 (IFGP4, IRTA4, SPAP1A (SH-12 domain containing phosphatase anchor protein 1a), SPAP1B, SPAP1C); (17) HER2; (18) NCA; (19) MDP; (20) IL20Ra; (21) Brevican; (22) EphB2R; (23) ASLG659; (24) PSCA; (25) GEDA; (26) BAFF-R (B cell-activating factor receptor, BLyS receptor 3, BR3); (27) CD22 (B-cell receptor CD22-B isoform); (28) CD79a (CD79A, CD79a, immunoglobulin-associated alpha); (29) CXCR5 (Burkitt's lymphoma receptor 1); (30) HLA-DOB (MHC, Beta subunit of MHC class II molecule (Ia antigen)); (31) P2X5 (urinergic receptor P2X ligand-gated ion channel 5); (32) CD72 (B-cell differentiation antigen CD72, Lyb-2); (33) LY64 [Lymphocyte antigen 64 (RP105), type I membrane protein of the leucine rich repeat (LRR) family]; (34) FcRH1 (Fc receptor-like protein 1); (35) IRTA2 (Immunoglobulin superfamily receptor translocation associated 2); (36) TENB2 (putative transmembrane proteoglycan); (37) HGF, EGFR, EGFRvIII, Her2, Her3, IGF-1R, VEGF, VEGFR-1, VEGFR-2, VEGFR-3, Ang2, DII4, NRP1, FGFR, FGFR2, FGFR3, c-Kit, MUC1, MUC16, CD20, CD22, CD27, CD30, CD33, CD40, CD52, CD70, CD79, DDL3, Folate R1, Nectin 4, Trop2, gpNMB, Axl, BCMA, PD-1, PD-L1, PD-L2, CTLA4, BTLA, 4-1BB, ICOS, GITR, OX40, VISTA, TIM-3, LAG-3, KIR, B7.1, B7.2, B7-H2, B7-H3, B7-H4, B7-H6, B7-H7, EphA2, EphA4, EphB2, E-selectin, EpCam, CEA, PSMA, PSA, c-MET etc.; and (38) TCR/CD3, CD16(Fcγ RIIIa) CD44, CD56, CD69, CD64(Fcγ RI), CD89, CD11b/CD18(CR3) as immune effector cell-related antigens.

In an embodiment of the present disclosure, the antibody may include any antibody without limitation as long as it can be used to prevent and treat proliferative diseases and particularly to treat cancers. For example, the antibody may include one selected alemtuzumab, apolizumab, aselizumab, atlizumab, bapineuzumab, bevacizumab, bivatuzumab mertansine, cantuzumab mertansine, cedelizumab, certolizumab pegol, cetuximab, cidfusituzumab, cidtuzumab, daclizumab, eculizumab, efalizumab, epratuzumab, erlizumab, ertumaxomab, felvizumab, fontolizumab, gemtuzumab, gemtuzumab ozogamicin, ibritumomab tiuxetan, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, panitumumab, pascolizumab, pecfusituzumab, pectuzumab, pertuzumab, pexelizumab, ralivizumab, ranibizumab, reslivizumab, reslizumab, resyvizumab, rituximab, rovelizumab, ruplizumab, sibrotuzumab, siplizumab, sontuzumab, tacatuzumab tetraxetan, tadocizumab, talizumab, tefibazumab, tocilizumab, toralizumab, tositumomab, trastuzumab, tucotuzumab celmoleukin, tucusituzumab, umavizumab, urtoxazumab, and visilizumab, but may not be limited thereto.

In an embodiment of the present disclosure, the linker is generally used in the art, and the linker useful for an antibody-drug conjugate may be used without limitation and may include one selected from the followings, but may not be limited thereto:

bis-maleimidopolyethyleneglycol (BMPEO), N-(β-maleimidopropyloxy)succinimide ester (BMPS), ε-maleimidocaproic acid N-hydroxysuccinimide ester (EMCS), γ-maleimidobutyric acid N-succinimidyl ester (GMBS), HBVS, long chain N-succinimidyl 4-(maleimidomethyl)cyclohexanecarboxylate (SMCC), m-maleimidobenzoyl-N-hydroxysuccinimide ester (MBS), 4-(4-N-maleimidophenyl)-butyric acid hydrazide (MPBH), N-succinimidyl 3-(bromoacetamido)propionate (SBAP), N-succinimidyl iodoacetate (SIA), N-succinimidyl-4-(iodoacetyl)-aminobenzoate (SIAB), N-succinimidyl 4-(maleimidomethyl)cyclohexanecarboxylate (SMCC), N-succinimidyl 4-(p-maleimidophenyl)butyrate (SMPB), succinimidyl-6-(maleimidopropionamido)hexanoate (SMPH), N-(ε-maleimidocaproyloxy)sulfosuccimido ester (sulfo-EMCS), N-(γ-maleimidobutryloxy)sulfosuccinimde ester (sulfo-GMBS), N-(κ-maleimidoundecanoyloxy)sulfosuccinimide ester (sulfo-KMUS), m-maleimidobenzoyl-N-hydroxysulfosuccinimide ester (sulfo-MBS), sulfosuccinimidyl(4-iodo-acetyl)aminobenzoate (sulfo-SIAB), sulfosuccinimidyl 4-(N-maleimido-methyl)cyclohexane-1-carboxylate (sulfo-SMCC), sulfosuccinimidyl 4-(p-maleimidophenyl)butyrate (sulfo-SMPB), and succinimidyl-(4-vinylsulfone)benzoate (SVSB); and bis-maleimide reagents: dithiobis-maleimidoethane (DTME), 1,4-bis-maleimidobutane (BMB), 1,4-bis-maleimidyl-2,3-dihydroxybutane (BMDB), bis-maleimidohexane (BM H), bis-maleimidoethane (BMOE), 1,8-bis-maleimidodiethyleneglycol [BM(PEO)$_2$], and 1,11-bis-maleimidotriethyleneglycol [BM(PEO)$_3$]; and having highly potent anticancer effect with IC$_{50}$ to cancer cells in the range of nM or pM, but may not be limited thereto.

In an embodiment of the present disclosure, the linker and the benzoselenophene-based compound may be linked by a peptide bond, but may not be limited thereto.

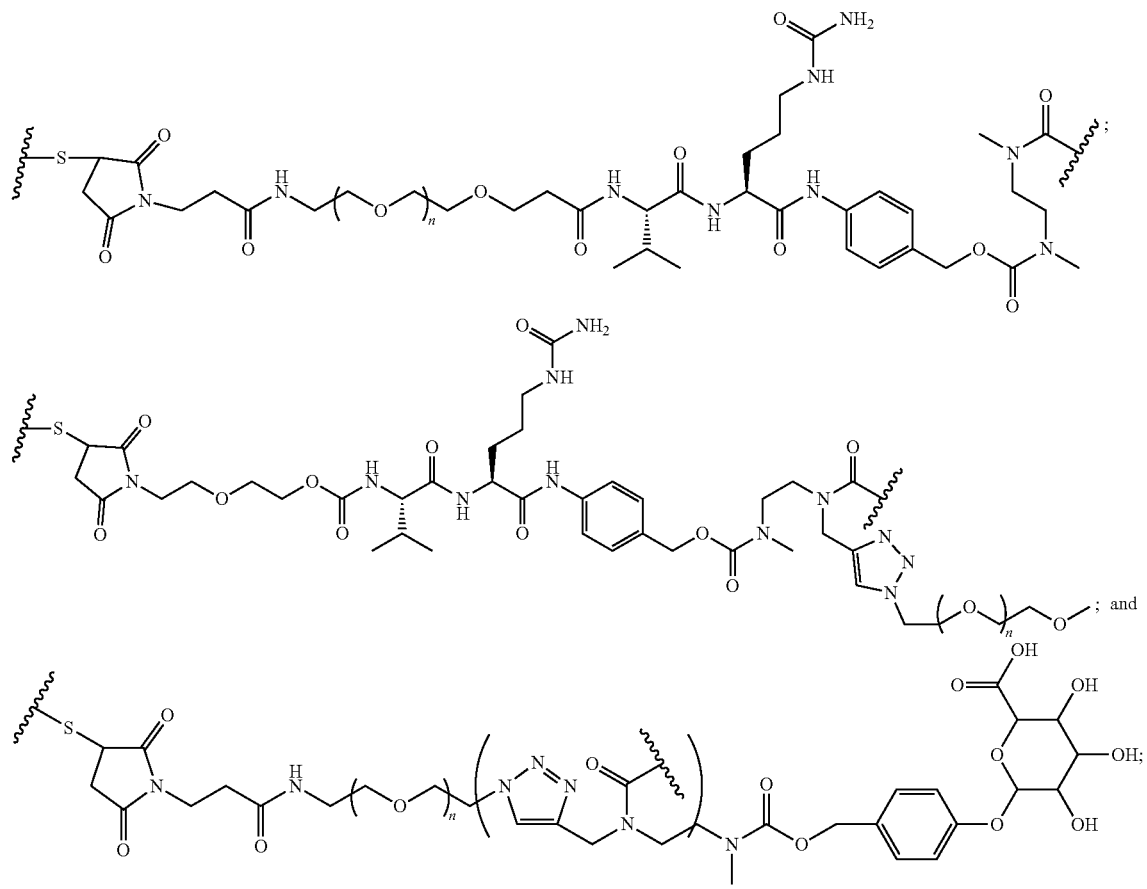

in the above linkers, each of broken lines may indicate a covalent bond to the antibody or the benzoselenophene-based compound, and n may be 1 to 1,000.

In an embodiment of the present disclosure, n may be about 1 to about 1,000, about 1 to about 900, about 1 to about 800, about 1 to about 700, about 1 to about 600, about 1 to about 500, about 1 to about 400, about 1 to about 300, about 1 to about 200, about 1 to about 100, about 1 to about 50, about 1 to about 40, about 1 to about 30, about 1 to about 20, about 1 to about 10, about 1 to about 5, or about 1 to about 3, but may not limited thereto. In an embodiment of the present disclosure, n may be about 1 to about 5, or about 1 to about 3.

In an embodiment of the present disclosure, by adjusting n number of polyethylene glycol (PEG) of the linker, for example, to form PEG with a molecular weight of about 1,000 or about 2,000 or to form 4-arm or 8-arm branched PEG, a DNA alkylating derivative containing a benzoselenophene-based compound with increased water solubility can be synthesized and used as an anticancer drug or a precursor thereof, but may not be limited thereto.

In an embodiment of the present disclosure, the antibody-drug conjugate of the present disclosure may be a substance In an embodiment of the present disclosure, if the functional groups are substituted, the substituents may include one or more members selected from an acyl group, an amino group (including mono- and dialkylamino groups, mono- and diarylamino groups and an alkylarylamino group), an acylamino group (including a carbamoyl and a ureido group), an alkylcarbonyloxy group, an arylcarbonyloxy group, an alkoxycarbonyloxy group, an alkoxycarbonyl group, a carboxyl group, a carboxylate group, an aminocarbonyl group, mono- and dialkylaminocarbonyl groups, a cyano group, an azido group, a halogen group, a hydroxyl group, a nitro group, a trifluoromethyl group, a thiol group, an alkylthiol group, an arylthiol group, an alkylthiocarbonyl group, a thiocarboxylate group, a low-grade alkyl group, a low-grade alkenyl group, a low-grade alkynyl group, a cycloalkyl group, a heterocycloalkyl group, an aryl group, a heteroaryl group, a low-grade alkoxy group, an aryloxy group, an aryloxycarbonyloxy group, a benzyloxy group, a benzyl group, a sulfinyl group, an alkylsulfinyl group, a sulfonyl group, a sulfate group, a sulfonate group, a sulfonamide group, a phosphate group, a phosphonate group, a phosphinato group, an oxo group, a guanidine group, an imino group and a formyl group, but may not be limited thereto.

In an embodiment of the present disclosure, $R^1$ may be a dialkylamino group including tertiary nitrogen, and each of $R^4$ and $R^5$ may be independently hydrogen, methyl or ethyl, but may not be limited thereto.

In an embodiment of the present disclosure, X may be F, Cl, Br or I, but may not be limited thereto. Further, in an embodiment of the present disclosure, X may be Cl.

In an embodiment of the present disclosure, a benzoselenophene-based compound of the present disclosure contains —$CHR^2CHR^1R^3$ linked to a benzoselenophene host by an amide bond and two sip' carbon atoms as a main framework and thus can be increased in flexibility of the molecules. Further, desirably, $R^1$ contains tertiary amine having a small substituent. For example, if $R^1$ is tertiary nitrogen, since its $pK_a$ is about 6, it functions as a weak base and exists in the form of a salt under physiological conditions, which may cause a great increase in water solubility.

In an embodiment of the present disclosure, $R^1$ includes dimethylamino, ethylmethylamino, diethylamino, methylpropylamino, ethylpropylamino or dipropylamino, but may not be limited thereto.

In an embodiment of the present disclosure, $R^1$ may be dimethylamino, ethylmethylamino, diethylamino.

In an embodiment of the present disclosure, both of $R^2$ and $R^3$ may be hydrogen.

In an embodiment of the present disclosure, each of $R^5$ and $R^6$ may be independently hydrogen, methyl, ethyl or propyl.

In an embodiment of the present disclosure, the benzoselenophene-based compound may include the following compound 2:

[Compound 2]

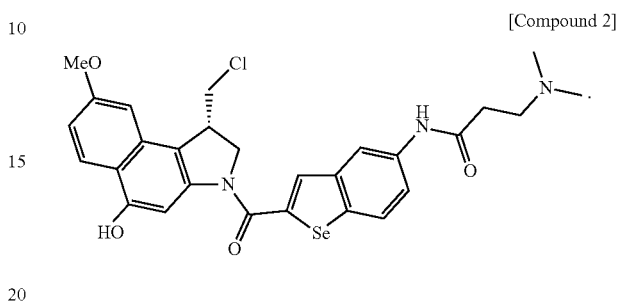

In an embodiment of the present disclosure, a bond of the benzoselenophene-based compound and the linker may be prepared by the following method as an example (Scheme A), but may not be limited thereto:

[Scheme A]

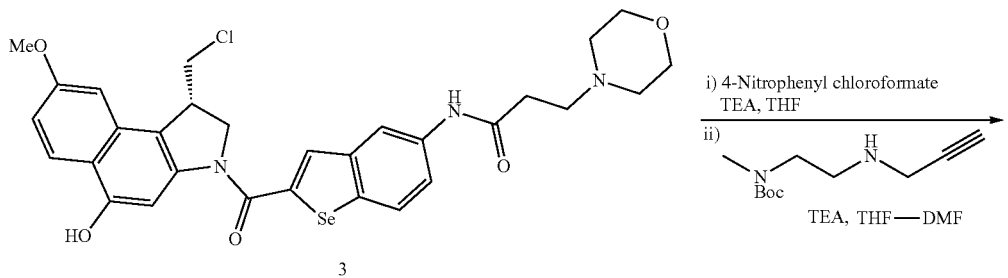

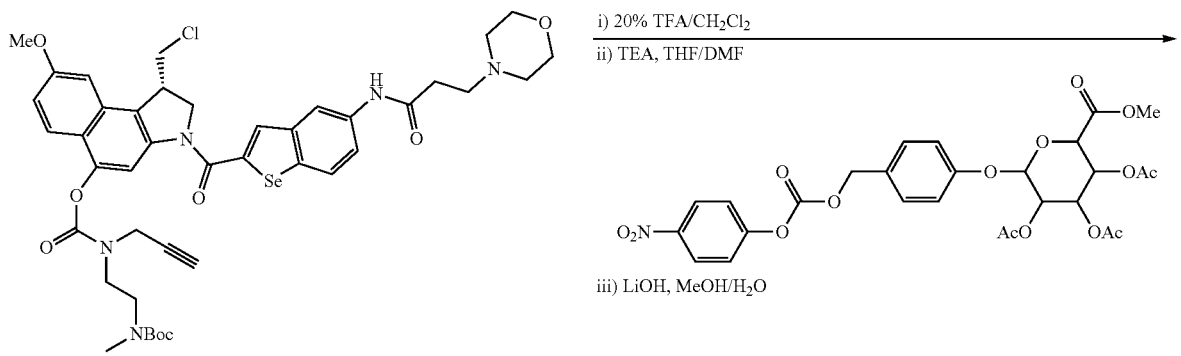

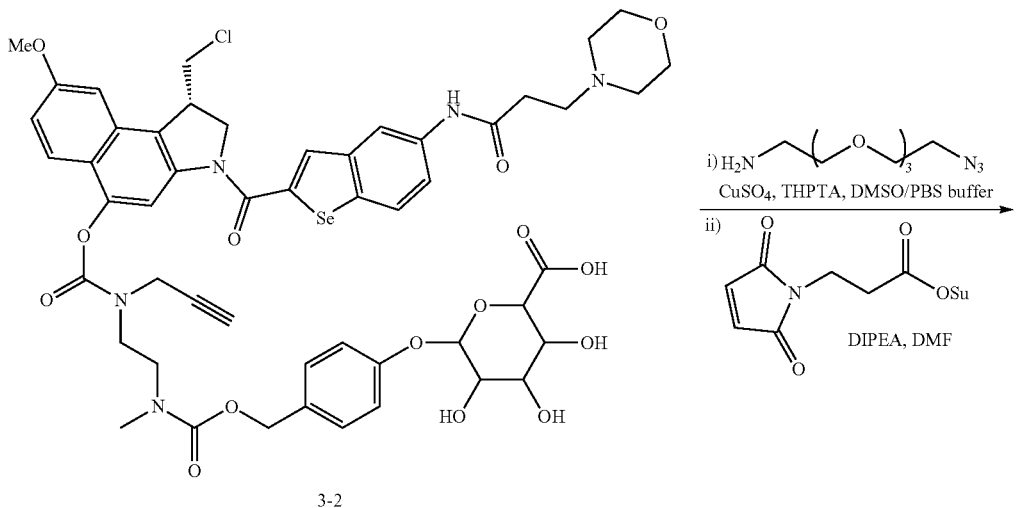

3-2

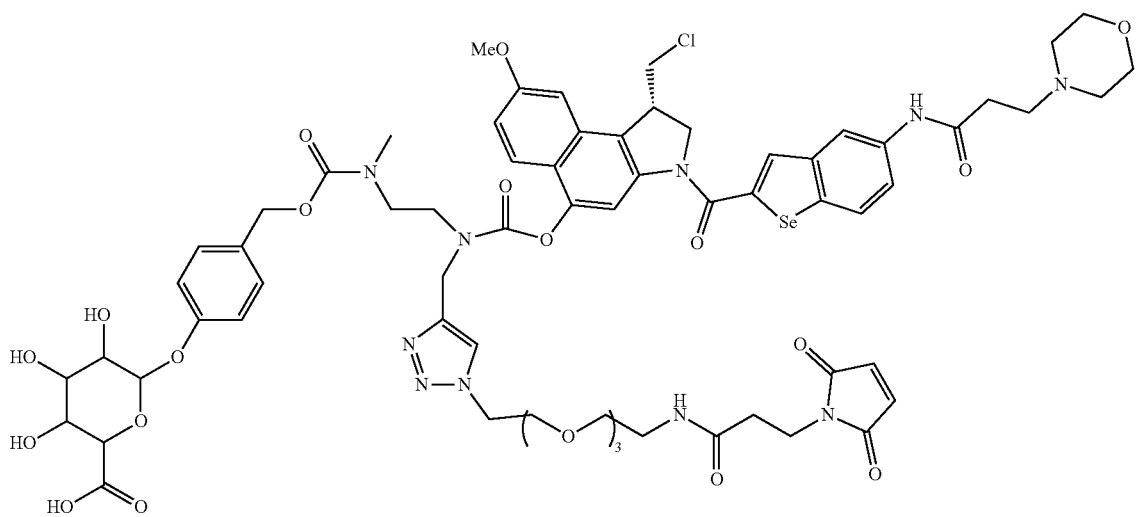

3-3

In an embodiment of the present disclosure, Drug-to-antibody ratio (DAR) of the antibody-drug conjugate may be about 1 to about 8, but may not be limited thereto. In an embodiment of the present disclosure, DAR of the antibody-drug conjugate may be about 1 to about 8, about 1 to about 6, about 1 to about 5, about 2 to about 8, about 2 to about 6, about 2 to about 5, about 3 to about 8, about 3 to about 6, or about 3 to about 5, but may not be limited thereto. Further, in an embodiment of the present disclosure, DAR of the antibody-drug conjugate may be about 2 to about 5.

A fifth aspect of the present disclosure provides an anticancer composition including the antibody-drug conjugate or a pharmaceutically acceptable salt thereof according to the fourth aspect.

Detailed descriptions on the fifth aspect of the present disclosure, which overlap with those on the first aspect to the fourth aspect of the present disclosure, are omitted hereinafter, but the descriptions of the first aspect to the fourth aspect of the present disclosure may be identically applied to the second aspect of the present disclosure, even though they are omitted hereinafter.

In an embodiment of the present disclosure, the anticancer composition may have anticancer activity to at least one selected from solid tumor, hematologic malignancy, calorectal cancer, uterine cancer, uterine myoma, meningioma, lung cancer, small cell lung cancer, gastrointestinal malignancy, colorectal cancer, intestinal cancer, breast cancer, ovarian cancer, prostate cancer, testis cancer, liver cancer, renal cancer, bladder cancer, pancreatic cancer, brain cancer, sarcoma, osteogenic sarcoma, Kaposi sarcoma and melanoma, but may not be limited thereto. A pharmaceutical composition according to an embodiment of the present disclosure can be applied to various diseases, not limited to cancers, as prevention or treatment targets.

Hereinafter, example embodiments are described in more detail by using Examples, but the present disclosure may not limited to the Examples.

EXAMPLES

1. Example 1 (Preparation of Compound 2, DS-26)

(1) Synthesis of Intermediate:

Preparation of 5-(3-(dimethylamino)propanamido)benzo[b]selenophene-2-carboxylic acid (Compound 6)

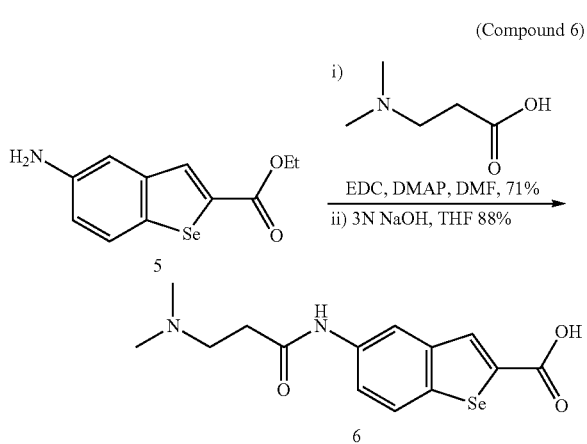

3-(dimethylamino)propanoic acid (3 eq), EDC (3 eq) and DMAP (2 eq) were dissolved in DMF and stirred for 15 minutes and then reacted with (ethyl)(5-amino-benzo[b]selenophene-2-carboxylate) (Compound 5, 1 eq) for 24 hours. After completion of the reaction, methylene chloride (MC)/water was used to separate an MC layer with a separatory funnel and then dried with MgSO4 and filtered. A solvent was removed from the filtrate by a rotary evaporator, followed by column chromatography. Yield: 71%.

$^1$H NMR (500.1 MHz, CDCl$_3$) δ 1.39 (t, 3H, J=7.2), 2.42 (s, 6H), 2.56 (t, 2H, J=5.8), 2.71 (t, 2H, J=5.7), 4.37 (q, 2H, J=7.1), 7.39 (d, 1H, J=8.6), 7.77 (d, 1H, J=8.6), 8.23 (s, 1H), 8.25 (s, 1H); $^{13}$C NMR (125.7 MHz, CDCl$_3$) δ 13.3, 32.3, 43.4, 54.1, 60.6, 116.8, 119.1, 124.9, 133.3, 135.4, 136.4, 137.6, 140.8, 162.9, 169.7; HRMS (ESI); m/z calcd for C$_{16}$H$_{20}$N$_2$O$_3$Se [M+]: 368.06; found: 369.0718 [M+H]+

(Ethyl)(5-(3-(dimethylamino)propanamido)benzo[b]selenophene-2-carboxylate) (1 eq) obtained in the above-described process was dissolved in methanol and then reacted with 2 mL of 3 N→M NaOH for 24 hours. After completion of the reaction, 20% HCl was added thereto to adjust pH to acid. Then, a solvent was removed by a rotary evaporator, followed by column chromatography. Yield: 88%.

$^1$H NMR (500.1 MHz, MeOD-d$_4$) δ 2.88-2.91 (m, 8H), 3.42 (t, 2H, J=6.4), 7.38 (d, 1H, J=8.6), 7.72 (d, 1H, J=8.6), 7.85 (s, 1H), 8.05 (s, 1H); $^{13}$C NMR (125.7 MHz, MeOD-d$_4$) δ 30.9, 42.1, 52.5, 117.1, 119.6, 126.4, 133.4, 136.6, 137.7, 139.8, 141.6, 168.0, 171.4; HRMS (ESI); m/z calcd for C$_{14}$H$_{16}$N$_2$O$_3$Se [M+]: 340.03; found: 341.0406 [M+H]+

(2) Preparation of Final Product by Reaction Between Intermediate and Seco-MCBI

By using a method known in the art, seco-MCBI (Compound 1) used for the synthesis was synthesized. A process for synthesizing Compound 2 by coupling benzoselenophene carboxylic acid to an intermediate obtained through an acid treatment was performed by the following method:

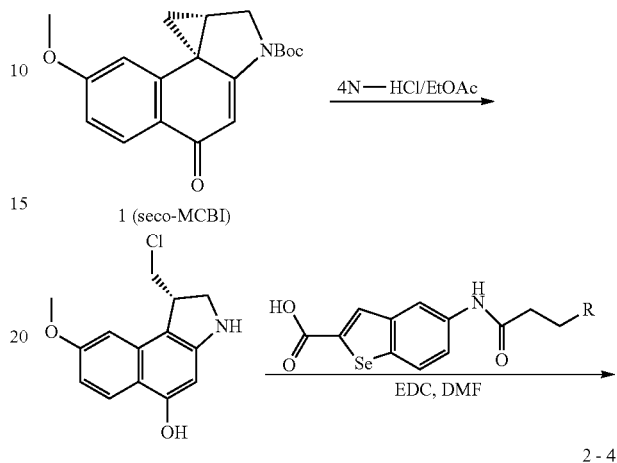

A reaction mixture was prepared by adding, at −78° C., 4 mL of HCl saturated solution in ethyl acetate into a round bottom flask containing seco-MCBI (Compound 1, 30 mg, 0.09 mmol). The reaction mixture was stirred at −78° C. for 30 minutes and then stirred at room temperature for 1 hour. After salt formation was observed from TLC, ethyl acetate was evaporated under nitrogen flux and then completely dried under high vacuum for 1 hour. The produced residue was dissolved in anhydrous DMF (0.2 mL) and added, at 0° C., to a mixture of carboxylic acid (1.1 eq) and EDC (52 mg, 0.27 mmol) represented as Compound 6 in anhydrous DMF (0.5 mL) and then stirred at 0° C. for 3 hours and stirred at room temperature for 5 hours. After completion of the reaction, the resultant product was diluted with water and extracted with ethyl acetate (3×15 mL). The obtained organic layer was washed with brine and dried with MgSO4, and filtered and concentrated to produce a crude product. The crude product was purified by column chromatography to obtain a desired product.

(3) Analysis Result of Compound 2

(S)—N-(2-(1-(chloromethyl)-5-hydroxy-8-methoxy-2,3-dihydro-1H-benzo[e]indole-3-carbonyl)benzo[b]selenophen-5-yl)-3-(dimethylamino)propanamide (Compound 2, DS-26)

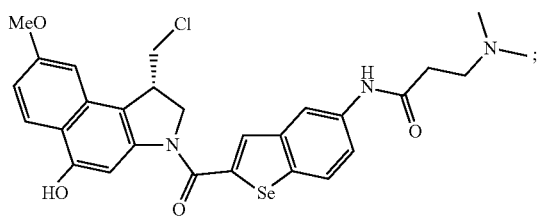

$^1$H NMR (500.1 MHz, Acetone-d6) δ 10.37 (s, 1H), 8.46 (s, 1H), 8.21 (d, J=6.9 Hz, 1H), 8.15 (d, J=9.2 Hz, 1H), 7.98 (d, J=8.6 Hz, 1H), 7.75 (brs, 1H), 7.52 (d, J=7.1 Hz, 1H), 7.21 (s, 1H), 7.03 (d, J=9.2 Hz, 1H), 4.75 (t, J=9.9 Hz, 1H), 4.66 (d, J=11.0 Hz, 1H), 4.21 (m, 1H), 4.06 (dd, J=11.0, 3.0 Hz, 1H), 3.96 (s, 3H), 3.83 (m, 1H), 2.80 (t, J=5.9 Hz, 2H), 2.60 (t, J=5.8 Hz, 2H), 2.41 (s, 6H); HRMS Calcd for ($C_{28}H_{28}ClN_3O_4Se$) 586.1006 [M+H]+, Observed 586.1006.

2. Anticancer Activity Assay of Compound 2

A cytotoxicity test for Compound 2 (DS-26) according to Example 1 and a compound having the same host framework according to Comparative Example 1 (DS-28) was performed:

Example 1

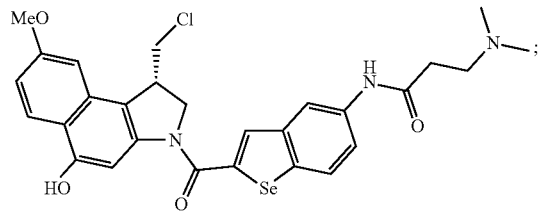 [SMILES: COc1ccc2c(O)cc3c(c2c1)[C@H](CCl)CN3C(=O)c1cc2cc(NC(=O)CCN(C)C)ccc2[se]1]

<Comparative Example 1> (DS-28)

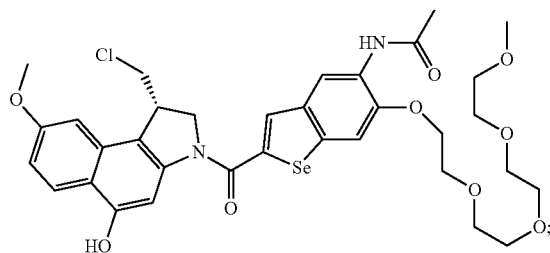 [SMILES: COCCOCCOCCOCCOc1cc2[se]c(C(=O)N3C[C@@H](CCl)c4c3cc(O)c3ccc(OC)cc43)cc2cc1NC(C)=O]

(1) Cell Cytotoxicity Assay

The present inventors treated a cancer cell line with drugs and then measured cell growth to evaluate cytotoxicity. Gastric cancer cells NCI-N87 were seeded in a 96-well at 3×104 cells per well. 4 hours later, the cells were treated with DS-26 (Example 1) and DS-28 (Comparative Example 1) at concentrations of 833.8 nM, 277.8 nM, 92.6 nM, 30.9 nM and 10.3 nM. 72 hours after treatment with drugs, the degree of cell growth was measured using an Ez-Cytox assay kit.

As a result, as shown in FIG. 1, it was confirmed that DS-26 (Example 1) exhibits potent cytotoxicity higher than the other drug.

(2) High-Throughput Screening (HTS)

The present inventors used an HTS system capable of screening various drugs or substances at once to further screen cytotoxicity of DS-26 (Example 1) and DS-28 (Comparative Example 1). Gastric cancer cells NCI-N87 and ovarian cancer cells SK-OV-3 were separately seeded in a 384-well and treated with drugs at various concentrations and cultured for 72 hours. Then, the degree of cell growth was measured by ATPlite assay. The measured data were converted into IC50 using GraphPad Prism 5.0 software, and area under the curve (AUC) was converted to analyze the titer of each drug.

According to the test result, as can be seen from the following Table 1, FIG. 2A, FIG. 2B, FIG. 3A and FIG. 3B, DS-26 had an $IC_{50}$ of from about 40 pM to about 50 pM and exhibits potent cytotoxicity. Also, DS-26 has stable solubility and stability in terms of chemical structure and thus considered worthy to be developed into drugs.

TABLE 1

| | | DS-26 | DS-28 |
|---|---|---|---|
| NCI-N87 | $IC_{50}$ (pM) | 5.55 | 5,860 |
| (HER+) | AUC | 477 | 689 |
| SK-OV-3 | $IC_{50}$ (pM) | 41.97 | 1,675 |
| (HER+) | AUC | 481 | 613 |

The above description of the example embodiments is provided for the purpose of illustration, and it would be understood by those skilled in the art that various changes and modifications may be made without changing technical conception and essential features of the example embodiments. Thus, it is clear that the above-described example embodiments are illustrative in all aspects and do not limit the present disclosure. For example, each component described to be distributed can be implemented in a combined manner.

The scope of the inventive concept is defined by the following claims and their equivalents rather than by the detailed description of the example embodiments. It shall be understood that all modifications and embodiments conceived from the meaning and scope of the claims and their equivalents are included in the scope of the inventive concept.

What is claimed is:

1. A benzoselenophene-based compound, represented by the following Chemical Formula 1:

[Chemical Formula 1]

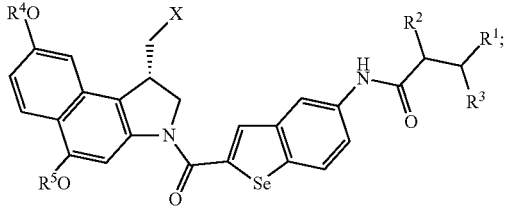

in the above Chemical Formula 1,
$R^1$ is a substituted or unsubstituted amino group, or a substituted or unsubstituted linear or branched $C_{1-6}$ alkylamino group,
each of $R^2$ and $R^3$ is independently hydrogen, fluorine, chlorine, bromine, iodine, or a substituted or unsubstituted $C_{1-5}$ alkyl group,
each of $R^4$ and $R^5$ is independently hydrogen, or a substituted or unsubstituted $C_{1-5}$ alkyl group, and
X is halogen.

2. The benzoselenophene-based compound of claim 1, wherein $R^1$ is a dialkylamino group including tertiary nitrogen, and
each of $R^4$ and $R^5$ is independently hydrogen, methyl or ethyl.

3. The benzoselenophene-based compound of claim 1, wherein $R^1$ includes dimethylamino, ethylmethylamino, diethylamino, methylpropylamino, ethylpropylamino or dipropylamino.

4. The benzoselenophene-based compound of claim 1, wherein the benzoselenophene-based compound is the following compound 2:

[Compound 2]

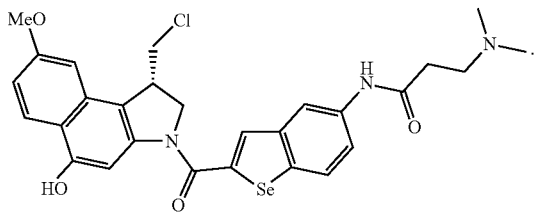

5. A pharmaceutical composition, comprising a benzoselenophene-based compound represented by the following Chemical Formula 1 or a pharmaceutically acceptable salt thereof, and the pharmaceutical composition is for preventing or treating proliferative diseases:

[Chemical Formula 1]

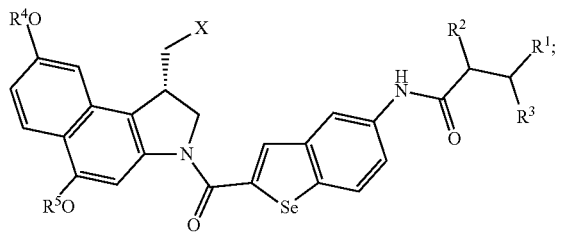

in the above Chemical Formula 1,
$R^1$ is a substituted or unsubstituted amino group, or a substituted or unsubstituted linear or branched $C_{1-6}$ alkylamino group,
each of $R^2$ and $R^3$ is independently hydrogen, fluorine, chlorine, bromine, iodine, or a substituted or unsubstituted $C_{1-5}$ alkyl group,
each of $R^4$ and $R^5$ is independently hydrogen, or a substituted or unsubstituted $C_{1-5}$ alkyl group, and
X is halogen.

6. The pharmaceutical composition of claim 5, wherein the benzoselenophene-based compound or a pharmaceutically acceptable salt thereof is a prodrug.

7. The pharmaceutical composition of claim 5, wherein the proliferative diseases include at least one selected from neoplasm, tumor, cancer, leukemia, psoriasis, bone diseases, fibroplasia disorders, and atherosclerosis.

8. The pharmaceutical composition of claim 7, wherein the cancer includes at least one selected from solid tumor, hematologic malignancy, calorectal cancer, uterine cancer, uterine myoma, meningioma, lung cancer, small cell lung cancer, gastrointestinal malignancy, colorectal cancer, intestinal cancer, breast cancer, ovarian cancer, prostate cancer, testis cancer, liver cancer, renal cancer, bladder cancer, pancreatic cancer, brain cancer, sarcoma, osteogenic sarcoma, Kaposi sarcoma and melanoma.

9. The pharmaceutical composition of claim 5, wherein $R^1$ is a dialkylamino group including tertiary nitrogen, and each of $R^4$ and $R^5$ is independently hydrogen, methyl or ethyl.

10. The pharmaceutical composition of claim 5, wherein $R^1$ includes dimethylamino, ethylmethylamino, diethylamino, methylpropylamino, ethylpropylamino or dipropylamino.

11. An antibody-drug conjugate or a pharmaceutically acceptable salt thereof, comprising:
an antibody;
a linker; and
a benzoselenophene-based compound represented by the following Chemical Formula 1 or its pharmaceutically acceptable salt thereof:

[Chemical Formula 1]

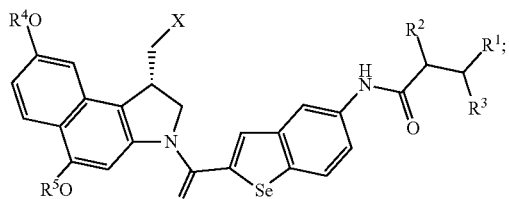

in the above Chemical Formula 1,
$R^1$ is a substituted or unsubstituted amino group, or a substituted or unsubstituted linear or branched $C_{1-6}$ alkylamino group,
each of $R^2$ and $R^3$ is independently hydrogen, fluorine, chlorine, bromine, iodine, or a substituted or unsubstituted $C_{1-5}$ alkyl group,
each of $R^4$ and $R^5$ is independently hydrogen, or a substituted or unsubstituted $C_{1-5}$ alkyl group, and
X is halogen.

12. The antibody-drug conjugate or a pharmaceutically acceptable salt thereof of claim 11, wherein the antibody-drug conjugate or a pharmaceutically acceptable salt thereof is a prodrug.

13. The antibody-drug conjugate or a pharmaceutically acceptable salt thereof of claim 11, wherein the antibody includes an antibody, an antibody variant or antigen-binding fragments thereof immunospecific to a proliferative disease.

14. The antibody-drug conjugate or a pharmaceutically acceptable salt thereof of claim 13, wherein the proliferative diseases include at least one selected from neoplasm, tumor, cancer, leukemia, psoriasis, bone disease, fibroplasia disorders, and atherosclerosis.

15. The antibody-drug conjugate or a pharmaceutically acceptable salt thereof of claim 14, wherein the cancer includes at least one selected from solid tumor, hematologic malignancy, colon cancer, rectal cancer, uterine cancer, myoma uteri, meningioma, lung cancer, small cell lung cancer, gastrointestinal malignancy, colorectal cancer, bowel cancer, breast cancer, ovarian cancer, prostate cancer, testis cancer, liver cancer, renal cell carcinoma, bladder cancer, pancreatic cancer, brain cancer, sarcoma, osteosarcoma, Kaposi's sarcoma and melanoma.

16. The antibody-drug conjugate or a pharmaceutically acceptable salt thereof of claim 11, wherein the antibody includes one selected from alemtuzumab, apolizumab, aselizumab, atlizumab, bapineuzumab, bevacizumab, bivatuzumab mertansine, cantuzumab mertansine, cedelizumab, certolizumab pegol, cetuximab, cidfusituzumab, cidtuzumab, daclizumab, eculizumab, efalizumab, epratuzumab, erlizumab, ertumaxomab, felvizumab, fontolizumab, gemtuzumab, gemtuzumab ozogamicin, ibritumomab tiuxetan, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, panitumumab, pascolizumab, pecfusituzumab, pectuzumab, pertuzumab, pexelizumab, ralivizumab, ranibizumab, reslivizumab, reslizumab, resyvizumab, rituximab, rovelizumab, ruplizumab, sibrotuzumab, siplizumab, sontuzumab, tacatuzumab tetraxetan, tadocizumab, talizumab, tefibazumab, tocilizumab, toralizumab, tositumomab, trastuzumab, tucotuzumab celmoleukin, tucusituzumab, umavizumab, urtoxazumab, and visilizumab.

17. The antibody-drug conjugate or a pharmaceutically acceptable salt thereof of claim 11,
wherein the linker includes one selected from bis-maleimidopolyethyleneglycol (BMPEO), N-(β-maleimidopropyloxy)succinimide ester (BMPS), ε-maleimidocaproic acid N-hydroxysuccinimide ester (EMCS), γ-maleimidobutyric acid N-succinimidyl ester (GMBS), HBVS, long chain N-succinimidyl 4-(maleimidomethyl)cyclohexanecarboxylate (SMCC), m-maleimidobenzoyl-N-hydroxysuccinimide ester (MBS), 4-(4-N-maleimidophenyl)-butyric acid hydrazide (MPBH), N-succinimidyl 3-(bromoacetamido)propionate (SBAP), N-succinimidyl iodoacetate (SIA), N-succinimidyl (iodoacetyl)-aminobenzoate (SIAB), N-succinimidyl 4-(maleimidomethyl)cyclohexanecarboxylate (SMCC), N-succinimidyl 4-(p-maleimidophenyl)butyrate (SMPB), succinimidyl (maleimidopropionamido)hexanoate (SMPH), N-(e-maleimidocaproyloxy)sulfosuccimido ester (sulfo-EMCS), N-(y-maleimidobutryloxy)sulfosuccinimde ester (sulfo-GMBS), N-(K-maleimidoundecanoyloxy) sulfosuccinimide ester (sulfo-KMUS), m-maleimidobenzoyl-N-hydroxysulfosuccinimide ester (sulfo-MBS), sulfosuccinimidyl(4-iodo-acetyl) aminobenzoate (sulfo-SIAB), sulfosuccinimidyl 4-(N-maleimido-methyl)cyclohexane-I-carboxylate (sulfo-SMCC), sulfosuccinimidyl 4-(p-maleimidophenyl) butyrate (sulfo-SMPB), and succinimidyl-(4-vinylsulfone)benzoate (SVSB); and bis-maleimide reagents: dithiobis-maleimidoethane (DTME), 1,4-bis-maleimidobutane (BMB), I,4-bismaleimidyl-2,3-dihydroxybutane (BMDB), bis-maleimidohexane (BMH), bis-maleimidoethane (BMOE), 1,8-bis-maleimidodiethyleneglycol [BM(PEO)₂], and 1,11-bis-maleimidotriethyleneglycol [BM(PEO)₃]; and

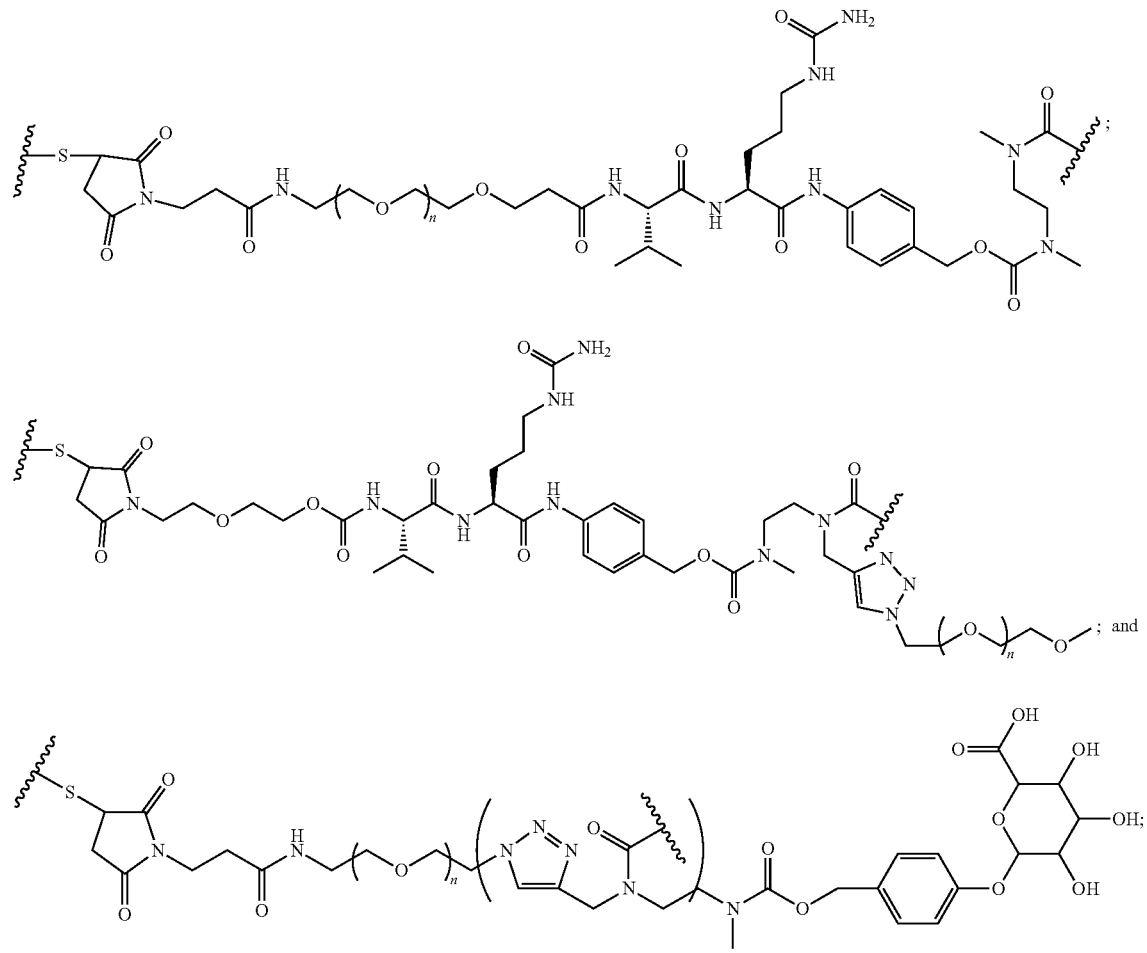

in the above,
wherein each of broken lines indicates a covalent bond to the antibody or the benzoselenophene-based compound, and n is 1 to 1,000.

18. The antibody-drug conjugate or a pharmaceutically acceptable salt thereof of claim 11,
wherein $R^1$ is a dialkylamino group including tertiary nitrogen, and
each of $R^4$ and $R^5$ is independently hydrogen, methyl or ethyl.

19. The antibody-drug conjugate or a pharmaceutically acceptable salt thereof of claim 11,
wherein $R^1$ includes dimethylamino, ethylmethylamino, diethylamino, methylpropylamino, ethylpropylamino or dipropylamino.

* * * * *